United States Patent [19]
Theroux et al.

[11] Patent Number: 5,869,775
[45] Date of Patent: Feb. 9, 1999

[54] SAMPLE REMOVING TOOL AND METHOD THEREOF

[75] Inventors: John F. Theroux, Westfield, Mass.; Frank J. Formanek, West Suffield, Conn.; Edward F. Lamoureux, Hampden, Mass.; Alfred D. Depeau, Somers, Conn.

[73] Assignee: Combustion Engineering, Inc., Windsor, Conn.

[21] Appl. No.: 856,818

[22] Filed: May 15, 1997

[51] Int. Cl.[6] ...................................................... G01N 1/04
[52] U.S. Cl. ........................ 73/864.41; 83/919; 219/69.2; 376/260
[58] Field of Search ...................................... 376/245, 249, 376/310, 260; 73/864.41, 864.51; 83/919; 219/60 R, 61.1, 69.2, 69.15

[56] References Cited

U.S. PATENT DOCUMENTS

| | | | |
|---|---|---|---|
| 5,317,607 | 5/1994 | Formanek | 376/260 |
| 5,408,883 | 4/1995 | Clark, Jr. et al. | 376/260 |
| 5,675,096 | 10/1997 | Hydeman et al. | 73/864.41 |

*Primary Examiner*—Daniel D. Wasil
*Attorney, Agent, or Firm*—Ronald P. Kananen; John H. Mulholland

[57] ABSTRACT

A pair of openings are formed using an EDM technique. A pair of clamps are inserted into the openings and moved toward each other until such time as the inboard edges of the two openings are engaged. A pair of EDM cutters are used to cut a pair of slots which extend from one opening to the other. Upon completion of these slots, the sample, which remains clamped between the two clamps, is withdrawn and lowered back down the conduit to a remote collection point.

5 Claims, 3 Drawing Sheets

SAMPLE REMOVING TOOL AND METHOD THEREOF

BACKGROUND OF THE INVENTION

1. Field of the Invention

This invention relates generally to a sampling technique. More specifically, this invention relates to a sampling technique which uses a tool that can be inserted into a conduit such as used in a nuclear facility, and used to cut out and remove a sample of the pipe wall for inspection and analysis.

2. Description of the Related Art

U.S. Pat. No. 5,317,607 issued on May 31, 1994 in the name of Formanek, discloses a tool having an EDM crack removal head which can be inserted and positioned with a nozzle/thermal sleeve and used to detect and then cut-away cracked portions of metal from the sleeve. While this arrangement has proven very useful, it suffers from the drawback that it is impossible for samples of the metal, which constitute the wall of the nozzle or sleeve, to be captured and returned to a remote site for further detailed inspection and analysis.

SUMMARY OF THE INVENTION

It is an object of this invention to provide a tool which can be inserted into a conduit such as tubing which extends from the transition zone up to the last support in 900 and 1300 Mwe steam generators such as are used in nuclear facilities, and used to cut-out and securely return a sample of tubing wall sufficient in size to allow meaningful inspection and analysis of the metal condition.

In brief, the above object is achieved using a technique wherein two spaced openings are formed using EDM cutting. A pair of clamps are then inserted into the openings and subsequently moved toward each other until such time as the inboard edges of the two openings are engaged. Following this step, a pair of EDM cutters, which can be used to form the two openings, are used to cut a pair of slots from one opening to the other. Upon completion of these slots, the sample, which is clamped between the two clamps is withdrawn and lowered back down the conduit to a remote collection point.

More specifically, a first aspect of the invention resides in a method of removing a sample of a conduit comprising the steps of: inserting a tool into a conduit; forming first and second openings in the conduit; inserting clamps into the openings; cutting two slots from the first opening to the second opening; using the clamps to support the piece of material which extends between the first and second openings and which is separated from the conduit by the cutting of the two slots; and removing the tool and the sample from the conduit.

A second aspect of the invention resides in an apparatus for removing a sample from a conduit comprising: means for inserting a tool into a conduit; means for forming first and second openings in the conduit; means for inserting clamps into the openings and for clamping edge portions of the openings; and means for cutting two openings which extend from the first opening to the second opening.

A third aspect of the invention resides in a tool for removing a sample of a conduit comprising: a pair of pawls which are adapted to be inserted through first and second openings formed in a conduit wall, and to clamp against edge portions of each opening; and a pair of cutting elements which are adapted to cut a pair of slots from the first opening to the second opening and to release a portion of the conduit wall which is clamped between the pair of pawls.

In more detail, the tube sample removal technique/tool according to the present invention is capable of cutting a segment of tubing from any tubesheet location up from the transitional zone to the last support in 900 and 1300 Mwe Steam Generators. Preferably the removed segment is a 45 to 60 degree annular sector between 20 and 30 mm in height. The opening remaining in the tube, after extracting the segment, is larger than the removed sample and can be approximately 90 degrees by 55 mm.

The cutting process is controlled to assure that consistent sample dimensions are maintained and that no mechanical loads are applied to the tube sample that could damage it in a manner that could affect the results of subsequent examinations of characterized defects of metallography.

The tooling provides a means for positively capturing the tube segment during the final cutting operation to assure that the sample will not inadvertently be lost on the steam generator secondary side. The tooling also maintains capture of the tube segment during the full length of removal from the primary side of the tube.

The cutting and removal process is capable of extracting a tube segment that straddles (i.e., is located in front of) a support plate. An eddy current coil is incorporated in the tool to identify and confirm the defect area when positioning the tool for the cut.

The equipment used to elevate and rotate the cutting tools is remotely operable and contains elevation and rotational position indications.

The sample removal process does not affect adjacent tubes and there are no chips or the possibility of greater than 10 micron diameter cutting fines generated during cutting operations.

BRIEF DESCRIPTION OF THE DRAWINGS

The various advantages and merits of the present invention will become more clearly appreciated as a detailed description of the preferred embodiment of the invention is given with reference to the appended drawings wherein.

DETAILED DESCRIPTION OF THE PREFERRED EMBODIMENT

FIGS. 1 to 6 show the sequence of operations which are conducted in order to provide maximum assurance that the steam generator tube segment is firmly captured.

Figure 1:
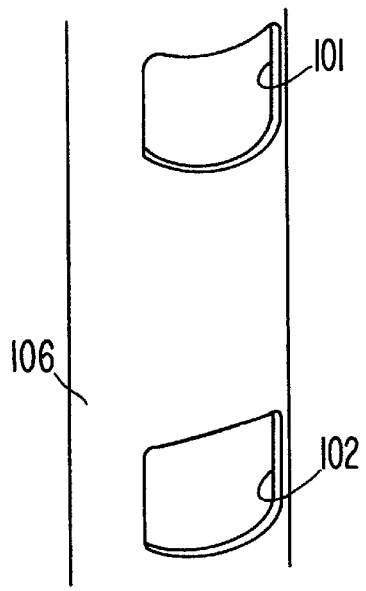
FIG. 1 is a perspective view showing two openings which have been formed in accordance with a first step of the inventive sampling technique.

FIG. 1 shows the first cuts wherein openings 101 and 102 are opened above and below the sample segment to be removed from a tube 106 using an EDM type window cutting tool. An example of such a type of tool can be found in the above mentioned U.S. Pat. No. 317,607 which is hereby incorporated by reference. It will be noted that in the arrangement illustrated in this patent, the EDM cutting tool is used only to remove a cracked portion of the tube wall; however, it will be readily apparent to those skilled in the art to which the present invention pertains that cutting all the way through the tube wall is simply a matter of adjustment.

Figure 2:
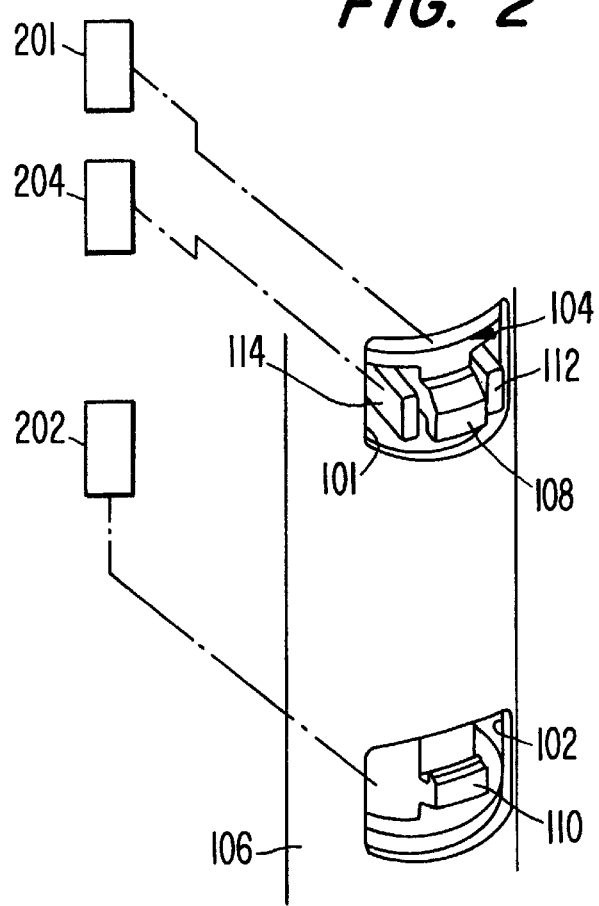
FIG. 2 is a perspective view showing a clamping and cutting tool being positioned with respect to the two openings in preparation for a clamping of a predetermined portion of the tube.

After the windows or holes are formed, the window cutting tool is removed and the extraction tool 104 installed within the tube 106. The extraction tool 104 will first grip the area between the windows 101, 102 that is to be removed using clamps or pawls 108, 110. Servo devices 201, 202 schematically illustrated as black boxes in FIG. 2, are used to control both lateral and vertical displacement of the pawls 108, 110.

Figure 3:
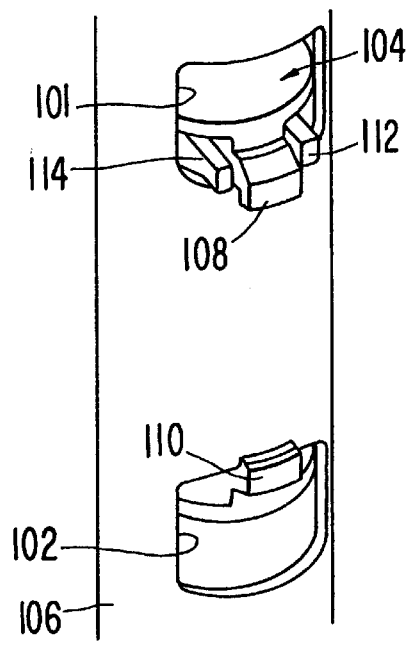
FIG. 3 is a perspective view showing the clamping tool being conditioned to clamp the clamp members against the inboard edges of the openings.
Figure 4:
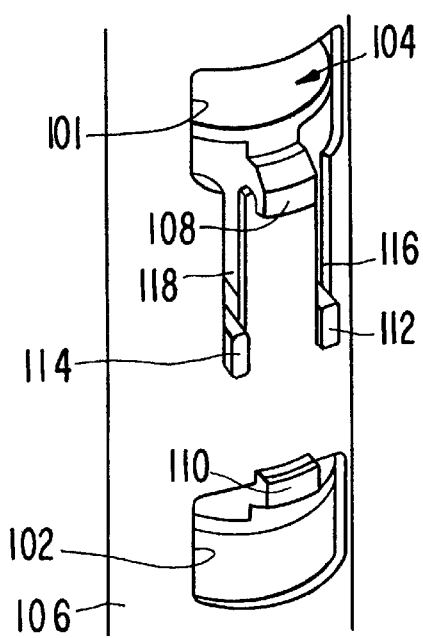
FIG. 4 is a perspective view showing the two EDM cutting elements cutting a pair of slots from one opening to the other.
Figure 5:
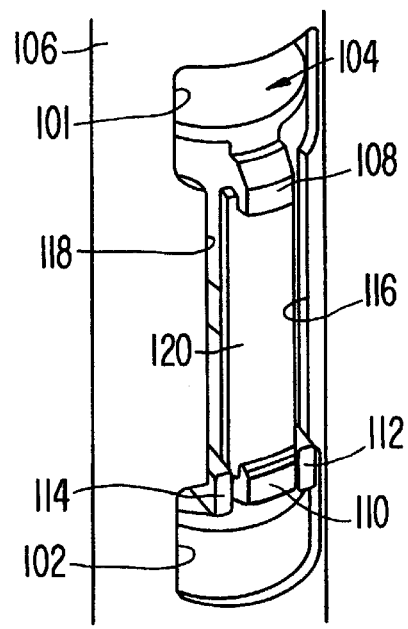
FIG. 5 is a perspective view showing the completion of the two slots and the tube sample being released and ready to be taken back down the conduit to a remote site.
Figure 6:
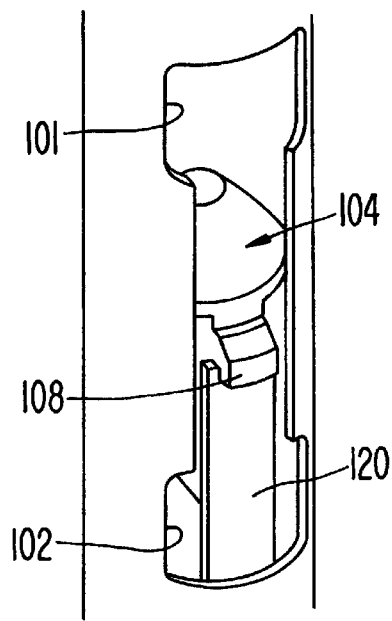
FIG. 6 is a perspective view showing the clamping and cutting tool being lowered back down the conduit toward the remote site at which the clamped sample will be collected.

After an acceptable grip, such as shown in FIG. 3, is confirmed, two slot cutting electrodes 112, 114, under the control of a servo mechanism 204, cut longitudinal slots 116, 118 in the area between the windows 101, 102, thereby freeing the approximately 60° and 30 mm (1.18 in.) long segment 120. Following this, the clamps 108, 110, the cutting electrodes 112, 114 and the sample segment 120 are withdrawn back into the tube 106. The extraction tool 104 is then lowered and the sample segment 120 is retracted back along the tube 106 and retrieved at a remote site such as a manway.

In accordance with the present invention, both cuts will be made using the Electrical Discharge Machining (EDM) process. The EDM process removes metal from a guide tube wall using high intensity electrical discharges or "sparks" that successively melt away minute amounts of material. The discharge occurs due to a DC voltage imposed between the guide tube 106 and the electrodes 108, 110. As the servo control system 204 modulates the electrode distance from the metal, a voltage gap is created across which the spark will jump. The contour of the opening or slot machined is in exact proportion to the electrode geometry with some minor differences due to electrode wear.

The EDM process offers the advantage of a repeatable tube segment geometry for purposes of subsequent testing. Since EDM applies no mechanical loads, there is also no concern the segment will be stressed or deformed during the removal process. The EDM process also produces an extremely small heat effected zone and there are no chips of metal, only very fine (~10 micron diameter) particles.

Although only one embodiment has been described, those skilled in the art to which this invention pertains will readily appreciate that various modifications and changes can be made without departing from the spirit of the invention which is limited only by the appended claims. For example, it is possible that the cutting electrodes, which are used to cut the slots necessary to remove the sample from the tube wall, can also be used to cut the windows in lieu of a separate window cutting tool. That is to say, by oscillating the cutting elements back and forth through a limited angle and slowly lowering the cutting elements in a kind of raster scan, the windows can be removed using the same EDM cutting technique used to form the slots.

Thus, for example, a tool can be inserted, a sensor used to determine a suitable sampling location, the cutting elements raised to a location suitable for the first window and the first window formed. The cutting elements can then be lowered by a predetermined amount and the second window formed. Thereafter the clamping elements can be extended through the windows and subsequently moved to their respective clamping positions. The cutting tools can then be used to form the slots which frees the sample from the tube wall.

What is claimed is:

1. A method of removing a sample of a conduit comprising the steps of:

inserting a tool into a conduit;

forming first and second openings in the conduit;

inserting clamps into the openings;

cutting two slots from the first opening to the second opening;

using the clamps to support a piece of material which extends between the first and second openings and which is separated from the conduit by the cutting of the two slots; and removing the tool and the sample from the conduit.

2. A method as set forth in claim 1, wherein said step of cutting two slots is carried using a pair of EDM cutting element.

3. An apparatus for removing a sample from a conduit comprising:

means for inserting a tool into a conduit;

means for forming first and second openings in the conduit;

means for inserting clamps into the openings and for clamping edge portions of the openings; and means for cutting two slots which extend from the first opening to the second opening.

4. An apparatus as set forth in claim 3, wherein said means for cutting two slots comprises a pair of EDM cutting elements.

5. A tool for removing a sample of a conduit comprising:

a pair of pawls which are adapted to be inserted through first and second openings formed in a conduit wall, and to clamp against edge portions of each opening; and a pair of cutting elements which are adapted to cut a pair of slots from the first opening to the second opening and to release a portion of the conduit wall which is clamped between the pair of pawls.

* * * * *

UNITED STATES PATENT AND TRADEMARK OFFICE
CERTIFICATE OF CORRECTION

PATENT NO. : 5,869,775
DATED : February 9, 1999
INVENTOR(S) : John F. THEROUX, Frank J. FORMANEK, Edward F. LAMOUREUX and Alfred D. DEPEAU It is certified that error appears in the above-identified patent and that said Letters Patent is hereby corrected as shown below:

The title, item [54] and col. 1, line 2 should read:

-- [54] SAMPLE REMOVING TOOL AND METHOD THEREFOR --

Signed and Sealed this

Sixth Day of July, 1999

*Attest:*

Q. TODD DICKINSON

*Attesting Officer*     *Acting Commissioner of Patents and Trademarks*